(12) United States Patent
Schneider et al.

(10) Patent No.: US 11,830,186 B2
(45) Date of Patent: Nov. 28, 2023

(54) METHOD FOR DESIGNING A DRILLING TEMPLATE

(71) Applicants: SIRONA DENTAL SYSTEMS GMBH, Bensheim (DE); DENTSPLY SIRONA INC., York, PA (US)

(72) Inventors: Sascha Schneider, Mühlta (DE); Frank Thiel, Ober-Ramstadt (DE); Axel Schwotzer, Groß-Gerau (DE)

(73) Assignee: DENTSPLY SIRONA INC., York, PA (US)

( * ) Notice: Subject to any disclaimer, the term of this patent is extended or adjusted under 35 U.S.C. 154(b) by 392 days.

(21) Appl. No.: 17/251,364

(22) PCT Filed: Jun. 17, 2019

(86) PCT No.: PCT/EP2019/065837
§ 371 (c)(1),
(2) Date: Dec. 11, 2020

(87) PCT Pub. No.: WO2019/243233
PCT Pub. Date: Dec. 26, 2019

(65) Prior Publication Data
US 2021/0256696 A1  Aug. 19, 2021

(30) Foreign Application Priority Data

Jun. 22, 2018 (DE) .......................... 102018210259.7

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0088* (2013.01); *A61C 9/0053* (2013.01);
(Continued)

(58) Field of Classification Search
CPC ....... G06T 7/0012; G06T 15/04; G06T 15/08; G06T 2207/20081; G06T 2207/20084;
(Continued)

(56) References Cited

U.S. PATENT DOCUMENTS 6,319,006 B1 * 11/2001 Scherer .................. A61C 1/084
433/215
2005/0170311 A1 * 8/2005 Tardieu .................. A61C 1/084
433/76
(Continued)

FOREIGN PATENT DOCUMENTS

CN  107440811 A   12/2017
DE  19952962 A1   5/2001
(Continued)

OTHER PUBLICATIONS

Chinese Office Action dated Jul. 1, 2021.
(Continued)

*Primary Examiner* — Van D Huynh
(74) *Attorney, Agent, or Firm* — DENTSPLY SIRONA INC.

(57) ABSTRACT

A method for designing a drilling template, wherein a dental situation is measured by means of a 3D surface measuring device and a 3D surface model of the dental situation is produced and/or measured by means of an X-ray device or an MRI device, wherein the dental situation is measured and a volume model of the dental situation is produced, the method comprising the steps of: applying an artificial neural network for machine learning (convolutional neural network; CNN) to the 3D surface model of the dental situation and/or the volume model of the dental situation and/or to an initial 3D model of the drilling template; and automatically producing a ready made 3D model of the drilling template.

19 Claims, 2 Drawing Sheets

(51) Int. Cl.
*A61C 9/00* (2006.01)
*G06T 15/04* (2011.01)
*G06T 15/08* (2011.01)

(52) U.S. Cl.
CPC .............. *G06T 15/04* (2013.01); *G06T 15/08* (2013.01); *G06T 2207/20081* (2013.01); *G06T 2207/20084* (2013.01); *G06T 2207/30036* (2013.01)

(58) Field of Classification Search
CPC ........... G06T 2207/30036; G06T 17/00; A61B 5/0088; A61B 5/0062; A61B 2018/20353; A61C 9/0053; A61C 1/082; A61C 3/02; A61C 9/0046; G06N 3/08; G06N 20/00
USPC ........................................................ 382/128
See application file for complete search history.

(56) References Cited

U.S. PATENT DOCUMENTS

| | | | | |
|---|---|---|---|---|
| 2012/0214121 | A1* | 8/2012 | Greenberg | A61B 6/14 433/213 |
| 2012/0225409 | A1* | 9/2012 | Baumann | A61C 1/084 433/214 |
| 2013/0144417 | A1* | 6/2013 | Pieper | A61C 1/084 700/98 |
| 2015/0238289 | A1* | 8/2015 | Wouters | G05B 15/02 700/98 |
| 2018/0049850 | A1* | 2/2018 | Gassler | A61C 13/0003 |
| 2021/0082184 | A1* | 3/2021 | Claessen | G06N 3/08 |

FOREIGN PATENT DOCUMENTS

| | | |
|---|---|---|
| DE | 102009008790 B3 | 5/2010 |
| EP | 1502556 A2 | 2/2005 |
| WO | 9932045 A1 | 7/1999 |
| WO | 2018195554 A1 | 10/2018 |
| WO | 2019067995 A1 | 4/2019 |

OTHER PUBLICATIONS

International Search Report; PCT/EP2019/065837; Sep. 16, 2019 (completed); dated Sep. 25, 2019.
International Preliminary Report on Patentability; PCT/EP2019/065837; Sep. 16, 2019 (completed); dated Sep. 25, 2019.
Written Opinion of the International Searching Authority; PCT/EP2019/065837; Sep. 16, 2019 (completed); dated Sep. 25, 2019.

* cited by examiner

METHOD FOR DESIGNING A DRILLING TEMPLATE

TECHNICAL FIELD

The invention relates to a method for designing a drilling template, wherein by means of a dental camera or a laboratory scanner a dental situation is measured and a 3D surface model of the dental situation is produced and/or by means of an X-ray device or an MRI device the dental situation is measured and a volume model of the dental situation is produced.

BACKGROUND OF THE INVENTION

Several methods for designing drilling templates are known from the prior art.

DE 199 52 962 A1 discloses a method for creating a drilling aid for a dental implant. The drilling aid is equipped with contact surfaces that match the occlusal surfaces of neighboring teeth and is placed on the neighboring teeth for exact positioning in relation to the jaw section. A guide hole is provided in the drilling aid to guide a drill of a handpiece. The position, dimensions, and alignment of the guide hole in the drilling template are determined by the planned implant drilling.

DE 10 2009 008 790 B3 discloses a drilling template having a guide sleeve for guiding an oral surgical drill. The drill can also be inserted into the guide sleeve when there is minimal space available if the latter has a slot in the circumferential surface thereof which runs obliquely with respect to the longitudinal axis of the sleeve. Such a guide sleeve also allows almost optimal guidance of the drill in the direction of the planned drilling axis.

DE 199 52 962 A1 discloses a method for creating a drilling aid for a tooth implant, wherein first an X-ray image of the jaw and then a three-dimensional optical measurement of the visible surface of the jaw and the teeth are performed. The measurement data sets from the X-ray image and the three-dimensional optical image are correlated with one another. Based on the available information, such as the type and position of the implant relative to the neighboring teeth, a template that rests on the neighboring teeth is planned and generated, thereby enabling the implant guide hole to be drilled exactly. The implant can be determined and positioned in a known manner on the basis of the X-ray data. On the basis of the information obtained about the surface structure, i.e., the occlusal surfaces of adjacent teeth, an implantation aid in the form of a drilling template can be ground out using a CAD/CAM unit. Using the measurement data, a CAD/CAM machine is able to manufacture the drilling template with the negative of the occlusal surfaces and a guide passage for the drill. A stop that determines the drilling depth is transferred to the drilling template.

WO 99/32045 A1 discloses a method for producing a dental drilling aid for implants. First, a three-dimensional computer image is modeled using a jaw image with reference to an impression surface. Then the position and the drilling depth of the drill holes are determined and a set of implant drill hole coordinates is fed into a computer-controlled production machine. By means of a precision tool, a drill guide base is prepared in the drill body for each of the previously fed-in bore hole coordinate sets with a bore hole position and bore hole orientation determined using the jaw section.

A drilling template and a method for producing said drilling template are known from EP 1 502 556 A2, wherein the drilling template has at least one through-hole for guiding through the drill, into which at least one first guide sleeve can be inserted. In a lower region, the guide sleeve has an outer diameter which substantially corresponds to the inner diameter of the through-hole. In an upper area, the guide sleeve has a larger outer diameter, so that the upper section is supported on the edge of the drilling template surrounding the through-hole.

A disadvantage of the above-mentioned methods for designing drilling templates is that they are designed in a complex manner by means of the user, virtually or by using impressions. Measurement inaccuracies or design errors on the part of the user can result in inaccuracies of fit of the drilling template. An inaccurate drilling template can consequently lead to an incorrect implant drilling that deviates from the planned implant drilling.

The object of the present invention is therefore to provide a method for designing a drilling template which, in a time-saving manner, designs a suitable 3D model of the drilling template.

SUMMARY OF THE INVENTION

The invention relates to a method for designing a drilling template, wherein by means of a 3D surface measuring device such as a dental camera or a laboratory scanner a dental situation is measured and a 3D surface model of the dental situation is produced and/or by means of an X-ray device or an MRI device the dental situation is measured and a volume model of the dental situation is produced. An artificial neural network for machine learning (convolutional neural network; CNN) is applied to the 3D surface model of the dental situation and/or the volume model of the dental situation and/or to an initial 3D model of the drilling template and automatically produces a ready made 3D model of the drilling template.

The dental drilling template can be any drilling template, such as a drilling template supported by the neighboring teeth for minimally invasive surgery and a drilling template supported by the jawbone for so-called open-flap surgery. In this case, the drilling template is supported by the other neighboring teeth of the respective jaw or is screwed to the jawbone by means of screws.

The drilling template is used to guide a drill to carry out a planned implant drilling for inserting an implant, as calculated in an implant plan. At a through-opening, a sleeve can be inserted into the through-opening, wherein the inner surface of the sleeve serves to guide the drill. During implant planning, the volume model of the jaw and a three-dimensional optical measurement of the visible surface of the jaw and the teeth in the form of a 3D surface model can be used to virtually determine an implant type and the implant position relative to the jaw. In particular, the exact position, the relative angle to the jaw and the depth of the implant drillings for inserting the implants are planned. The drilling template is intended to carry out one or more implant drillings, which can also be arranged to be skewed to one another.

In particular, anatomical structures within the jaw such as tooth roots, tooth nerves, and the course and thickness of the jawbone are taken into account.

Depending on the selected implant and the implant position, the drilling template is then designed depending on the 3D surface model of the dental situation and/or the volume model.

The neural network can thus automatically carry out the following steps: selection of a suitable implant type;

arrangement of the implant relative to the jaw, taking into account of anatomical structures such as tooth roots, tooth nerves, and jawbones; designing of a 3D model of the drilling template comprising at least one guide hole for at least one implant drilling for the implant to be inserted, taking into account the 3D surface model of the dental situation and the volume model.

A tooth-borne drilling template can include an impression of the neighboring teeth of the implantation site for support on the neighboring teeth. A guide bore can be designed to be flared. The guide bore can in particular be conical with an oval or circular base area. The sleeve can have a cylindrical sleeve part that fits into the through-opening.

In the case of drilling templates that are fixed to the jawbone by means of screws, the drilling template has additional openings for the screws in addition to the guide bores.

A drilling template with sleeves can have different sleeves for the same guide bore with different diameters to first drill a hole with the smallest diameter and then, by replacing the sleeve and the respective drill, drill further holes with increasing diameters until the desired diameter at the implant drilling is reached.

After performing the implant drilling, the drilling template can be used to guide the screwing-in of the implant into the implant drilling.

The drilling template can be produced automatically from a blank according to the designed 3D model of the drilling template, for example by means of a 3D printer or by means of a CAD/CAM process.

The dental camera can be any three-dimensional dental camera that is based, for example, on a strip projection method or a confocal measurement method. The dental situation can include the immediate vicinity of the restoration to be inserted or also a larger area around the restoration to be inserted. The measurement by means of the dental camera can take place from different directions, such as an occlusal direction, a lingual direction, a buccal direction or a labial direction. After the measurement with the dental camera, the 3D model of the dental situation is produced. Then the neural network for machine learning is applied to the 3D model of the dental situation. After the analysis of the 3D model of the dental situation, a 3D model of the drilling template is then automatically produced.

A neural network (CNN) is described in detail in the Wikipedia article "Convolutional Neural Network" with the link https://de.wikipedia.org/wiki/Convolutional_Neural_Network.

The following explains a method using a CNN.

A convolutional neural network (CNN), from the German for "folding neural network", is a feed-forward artificial neural network. It is a concept in the field of machine learning inspired by biological processes. Convolutional neural networks are used in numerous modern artificial intelligence technologies, primarily in the machine processing of image or audio data.

Basically, the structure of a classic CNN consists of a convolutional layer, followed by a pooling layer. In principle, this unit can be repeated any number of times; if it is repeated enough, deep convolutional neural networks are referred to, which fall into the field of deep learning.

The CNN learns from the fact that free parameters or classifiers of the convolution kernel for a layer and the weighting thereof are learned when calculating the next layer.

The 3D model of the dental situation is thus used as input to the CNN or machine learning system, which is trained using a collection of a plurality of 3D models of different dental situations.

In a further step, the 3D model of the dental situation is analyzed using the machine learning system and a 3D model of the respective component is proposed as output.

The machine learning system can consist of one or more CNN networks.

The classifiers or characteristics are therefore automatically defined and refined during the analysis of the training set. The automatically determined classifiers of a 3D model of a dental situation could, for example, be a total area of a preparation or the course of the preparation margin, or a combination of both.

The neural network can consist of several layers, for example, wherein simple classifiers such as edges, flat surfaces or areas of equal brightness are automatically identified in a first layer. The classifiers are automatically refined in a second layer. The classifiers in the second layer can be, for example, the relative arrangement of the edges to one another, the relative direction of the edges or the course of the edges. In the further layers, the classifiers are increasingly refined and thus become increasingly complex. In this way, the CNN network independently learns to automatically produce a suitable 3D model of the drilling template using the 3D model of the dental situation and the volume model of the dental situation as input parameters.

The advantage of a neural network is that the parameter values of the internal convolution filter and the further processing of the filter outputs are learned during the analysis of the training set and therefore no further user specification is necessary.

Another advantage of the method is that the drilling template is designed fully automatically by means of the neural network. This means that the component can be designed fully automatically immediately after the optical measurement and/or the X-ray or MRT measurement and, after a check by the dentist, can be produced fully automatically using a 3D printer or a CAD/CAM device, so that the drilling template can be used to produce implant drillings within one session.

Another advantage of the method is that ready made drilling templates produced by the user can be used in the training data set of the CNN, thus improving the acceptance rate of the initial suggestions for the components and the degree of automation of the designing.

A possible method for training or parameterizing the machine learning system consisting of one or more CNN networks is explained below. In the first step, a large number of known 3D surface models and volume models of dental situations are analyzed. Possible entered data or input data is generated. The input data is produced in such a way that all possible degrees of freedom are available in the input data. This is achieved, for example, by using data augmentation. For this purpose, the 3D models of the dental situations are rotated by the defined degrees of freedom and/or scaled along the degrees of freedom.

The neural network can advantageously be trained on the basis of a training data set, wherein the training data set contains manual changes of several initial 3D models of drilling templates of at least one user, wherein the manual changes are carried out manually by the user, for example using CAD tools, when designing the 3D model of the respective drilling template.

As a result, the neural network learns to apply the manual changes made by a specific user to an initial proposal for a 3D model of a component to complete the designing of the component. The initial proposal of a 3D model of the component can be selected, for example, using a library of several 3D models of components. When the neural network trained in this way is applied to an unknown 3D model of a dental situation, changes to the initial proposal that are usual for the respective user are then automatically carried out. The manual changes to the initial 3D model of the drilling template can be, for example, adapting the implant type, adapting the implant position relative to the jawbone, adapting the length of an implant drilling, adapting a stop of a guide bore, adapting the external dimensions of the drilling template, changing a hole diameter the guide bore, inserting contact control windows and/or attaching additional retaining elements.

So-called contact control windows are used for visual inspection by the user as to whether the drilling template is correctly placed and is resting on the contact surfaces.

Additional retaining elements can be, for example, undercuts or screws for fixing the drilling template relative to the respective jaw.

The neural network can advantageously be trained on the basis of a training data set, wherein the training data set contains several 3D surface models and/or volume models of the dental situations and the corresponding 3D models of the ready made drilling templates of at least one user.

The neural network learns from the comparison data between an initial 3D model and a ready made 3D model of the drilling template, as well as from the arrangements of the anatomical structures such as tooth roots, tooth nerves, and jawbones within the volume model relative to the ready made 3D model of the drilling template.

The neural network can advantageously be trained on the basis of a training data set, wherein the training data set contains several initial 3D models of the drilling templates and corresponding ready made 3D models of the drilling templates of at least one user.

The neural network thus learns from the comparison data between an initial 3D model of the drilling template and the corresponding ready made 3D model of the drilling template.

The training data set can advantageously only contain the data of one user or a group of experienced users.

There is a single training data set for each user or for a group of experienced users.

As a result, the neural network can be trained using a training data set from an individual user or a group of users. The users for the training data set can be selected according to various criteria, for example, such as professional experience. For example, only data from users who have at least three years of professional experience or who have carried out at least 100 cases in the design of drilling templates can be used for the training data set.

Before performing the present method, the user can manually define the type of drilling template and the positions of the implant drilling to be performed, for example by means of a selection menu. The type of drilling template can be, for example, a drilling template without drilling sleeves, a drilling template with drilling sleeves, a drilling template with screws for attachment to the jawbone, or a drilling template with a contact surface for anchoring to the neighboring teeth.

The neural network can advantageously remain unchanged after training on the basis of the training data set or new data can be added to the training data set so that the neural network can be trained further on the basis of the expanded training data set.

For inexperienced users in particular, it is advantageous not to change a trained neural network at the beginning. For experienced users, it is more advantageous to add their own data on the designing of the drilling template to a training data set so that the neural network is continuously trained and over time better meets the requirements of the respective user. Further training data is therefore added to the extended training data set.

The 3D surface model of the dental situation can advantageously have at least one area for an implant supply with implants to be inserted, at least one neighboring tooth and/or an implant-supported mesostructure, such as an abutment.

The 3D model of the respective drilling template is therefore automatically designed by the neural network depending on the structures contained in the 3D model of the dental situation.

Advantageously, the neural network can automatically define a suitable material, a production method and/or an insertion method for the drilling template to be produced.

The suitable material can be, for example, a special plastic or a combination of different plastics. The production process can be, for example, production by means of a 3D printer or CAD/CAM process. The method of insertion can be, for example, fastening the drilling template by means of screws or by placing the drilling template on the neighboring teeth.

The training data set can advantageously also contain a material of the drilling template, a production process and/or an insertion method for the drilling template.

As a result, the training data set contains further essential information about the drilling template, so that the trained neural network can design a suitable drilling template that meets the requirements of the respective user.

In the case of designing a drilling template with drilling sleeves, the training data set can advantageously also contain a position, a shape and/or a type of the drilling sleeves.

As a result, the training data set contains essential information relating to the drilling sleeves, so that the trained neural network selects and positions the drilling sleeves as desired by the user.

The training data set can advantageously also contain a shape and/or position of at least one support structure or holding structure of the drilling template to be produced.

As a result, the training data set contains essential information relating to a support structure or holding structure.

The support structure can, for example, be a contact surface for placing on the neighboring teeth of the implantation area. The support structure can be shaped, for example, in the form of an impression of the neighboring teeth to ensure precise positioning of the drilling template relative to the jaw.

The training data set can advantageously also contain a shape and/or position of an anchoring structure for the drilling template to be produced.

As a result the training data set contains essential information regarding the anchoring structure, such as screws that fix the drilling template to the jawbone, so that the neural network can automatically select the anchoring structure and position it relative to the jawbone.

The training data set can advantageously also contain undercuts for anchoring the drilling template and/or additional holes with screws for fixing the drilling template.

As a result, the training data set contains additional information regarding several undercuts for anchoring the drilling template and/or with regard to additional holes for screws for fixing the drilling template to the jawbone, so that the neural network can independently design the undercuts of the drilling template or the additional holes for the screws. The undercuts on the drilling template are designed in such a way that the undercuts grip around the molars, for example, and the drilling template is thereby fixed when it is placed on the teeth.

Advantageously, the training data set can additionally contain at least one guide bore in the drilling template for an implant drilling to be produced and/or a contact area for supporting or fixing the drilling template and/or a screw for fixing the drilling template.

As a result, the training data set contains additional information relating to the guide bore or the contact area, so that the neural network can automatically define the position and orientation of the guide bore on the drilling template or can define the shape and arrangement of the contact area on the drilling template. The guide bore of the drilling template is used to guide an implant drill when performing an implant drilling. The guide bore can be provided with a drilling sleeve.

The training data set can advantageously also contain anatomical structures in the volume model, namely jawbones, tooth roots and/or tooth nerves, which are taken into account when designing an implant drilling.

As a result, the training data set contains additional information with regard to essential anatomical structures for planning an implant drilling, so that the neural network can automatically design an implant drilling taking these structures into account.

The neural network can advantageously take into account an ethnic group and/or a character type of the patient.

Characteristic anatomical features of an ethnic group can thereby be taken into account when designing the drilling template. The characteristic features of an ethnic group can, for example, be a characteristic tooth position.

Another object of the following invention is a device for data processing, including a device for performing the method according to the invention. The device for data processing can comprise a computer chip and can be, for example, a computer or a smartphone.

BRIEF DESCRIPTION OF THE DRAWINGS

The invention is explained with reference to the drawings. It can be seen that.

DETAILED DESCRIPTION OF THE INVENTION

Figure 1:
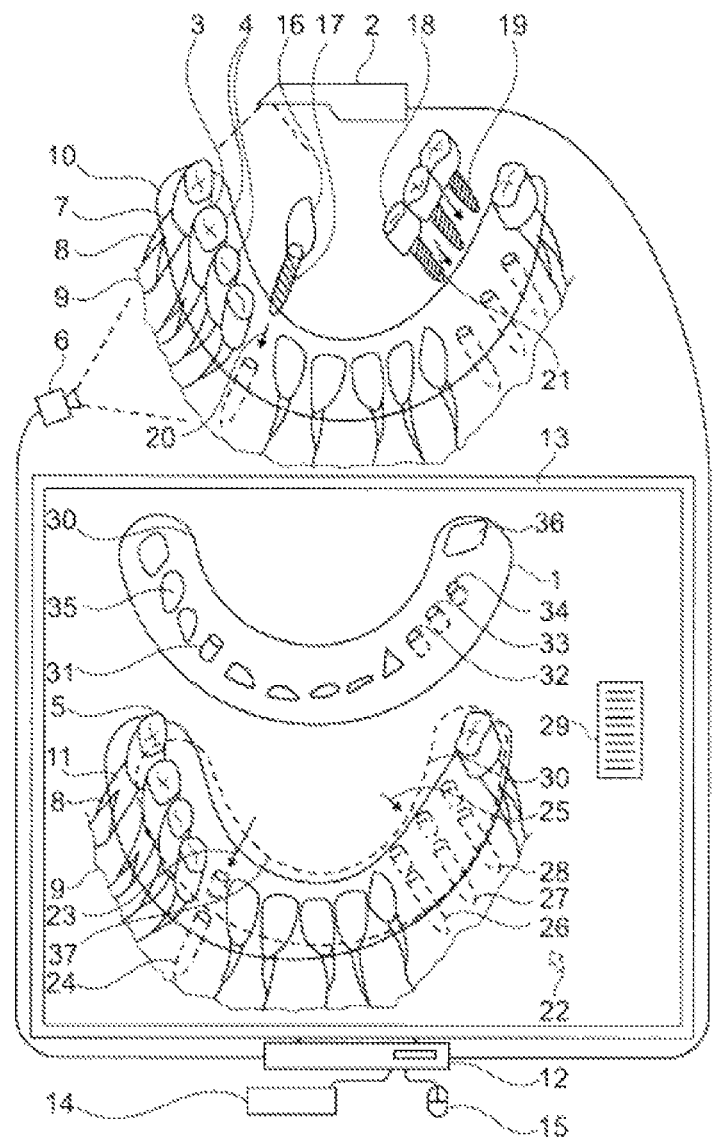
FIG. 1 shows a sketch to illustrate the method for designing the drilling template.

FIG. 1 shows a sketch to illustrate the method for designing a drilling template 1, wherein by means of a dental camera 2 a dental situation 3, comprising teeth 4, is measured and a 3D surface model 5 of the dental situation 3 is produced. In addition, by means of a CT X-ray device 6 or an MRI device a volume 7 comprising tooth roots 8, tooth nerves 9 and a jawbone 10 is measured and a volume model 11 of the dental situation 3 is produced. The image data from the dental camera 2 is forwarded to a computer 12, wherein the image data from the CT X-ray device 6 or the MRI device is also forwarded to the computer 12. The 3D surface model 5 and the volume model 11 are produced from this image data by means of the computer 12 and are displayed by means of a display device 13, such as a monitor. Input means such as a keyboard 14 and a mouse 15 are connected to the computer 12 to enable the user to navigate by means of a cursor 22 within a graphical representation of the 3D surface model 5 and the volume model 11. The dental situation 3 has a missing canine tooth and three missing molars. An implant-supported full crown 16 with an implant 17 is intended to replace the missing canine tooth, wherein an implant-supported bridge 18 made of three artificial molars and the associated implants 19 is to replace the missing molars, as indicated by arrows 20 and 21. In a first step, the user can manually define approximately a first position 23 of a first implant drilling 24 and approximately a second position of the bridge 18 to be inserted and thus a second implant drilling 26, a third implant drilling 27 and a fourth implant drilling 28, using the cursor 22. In a further step, the type of drilling template to be designed can be selected by means of the cursor 22 using a selection menu 29, namely a drilling template with or without drilling sleeves, a drilling template with anchoring to the jaw by screws or by a contact surface for the neighboring teeth. In a further step, a 3D model 30 of the drilling template is automatically produced by means of the neural network, which was trained on the basis of a training data set for the respective user and for the respective type of drilling template. The produced 3D model of the drilling template 1 has a first guide bore 31 for the first implant drilling 24, a second guide bore 32 for the second implant drilling 26, a third guide bore 33 for the third implant drilling 27 and a fourth guide bore 34 for the fourth implant drilling 28. In addition, the 3D model 30 of the drilling template 1 has a first contact surface 35 and a second contact surface 36 for anchoring the drilling template to the jaw, wherein the contact surfaces 35 and 36 can comprise parts of the negative impressions of the teeth 4 of the dental situation 3. The guide bores 31, 32, 33, and 34 can have drilling sleeves for guiding a corresponding implant drill. When defining the position and alignment of the individual implant drillings 24, 26, 27, and 28, the neural network takes into account essential anatomical structures, such as tooth roots 8, tooth nerves 9 and the jawbone, from the volume model 11. The neural network can learn, for example, that the implant drilling 24 must not damage the nerve 9. The neural network can automatically define the diameter and the length of the implant drillings 24, 26, 27, and 28, whereby mechanical loads on the full crown 16 to be inserted and the bridge 18 can be taken into account. In the graphic representation on the display device 13, the 3D model 30 of the drilling template 1 is shown in the inserted state relative to the 3D surface model 5 and the volume model 11 by a dashed line 37. Using the defined position, diameter, and length of the implant drillings 24, 26, 27, and 28, the neural network can define the position and the diameter of the corresponding guide bores 31, 32, 33, and 34 of the drilling template 1. The ready made 3D model 30 of the drilling template 1 can then be produced automatically by means of an automated method, such as a 3D printer or a CAD/CAM method.

Figure 2:
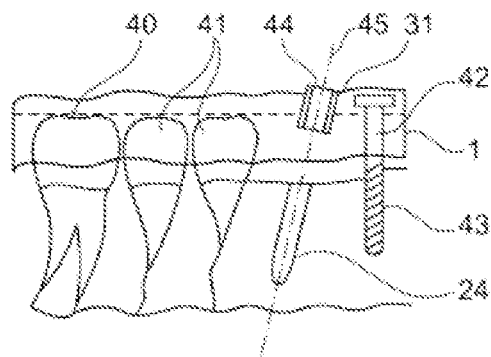
FIG. 2 shows a sketch of the drilling template with a drilling sleeve and a screw for fixing.

FIG. 2 shows a sketch of the drilling template 1 for performing the first implant drilling 24 from FIG. 1, wherein the drilling template 1 is anchored to the neighboring teeth 41 by means of a contact surface 40 and to the jaw 43 by means of a screw 42. The guide bore 31 has a drilling sleeve 44 for guiding an implant drill. The central axis 45 of the implant drilling 24 thus corresponds to the central axis of the drilling sleeve 44. The contact surface 40 can also be shaped as a negative impression of the teeth 41.

Figure 3:
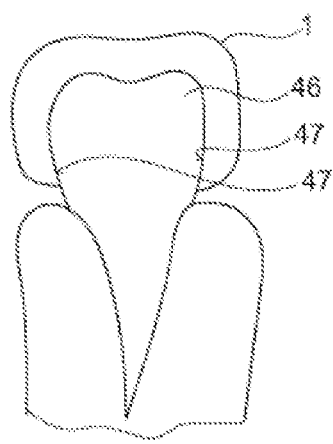
FIG. 3 shows a sketch of the drilling template with undercut for anchoring to the teeth.

FIG. 3 shows a sketch of a cross-section of the template 1, which is placed on the molars 46. The drilling template has two undercuts 47 in the lower area, so that when the drilling template 1 made of flexible plastic is placed on the molars 46, mechanical anchoring of the drilling template 1 to the teeth 46 is produced.

Figure 4:
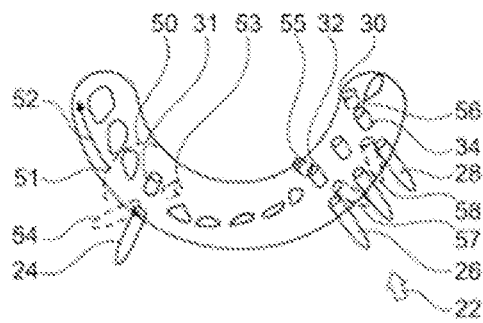
FIG. 4 shows a sketch of the changes by a user.

FIG. 4 shows a sketch of the ready made 3D model 30 of the drilling template 1 from FIG. 1, wherein starting from an initial proposal 50 of a 3D model of the drilling template, represented by a dashed line, the user has changed or adjusted the initial proposal 50 by manual changes by means of cursor 22 to obtain the ready made 3D model 30. The initial suggestion 50 has external dimensions 51 which have been enlarged by the user, as indicated by the arrow 52, to obtain the external dimensions of the 3D model 30. The initial proposal 50 has a first initial guide bore 53 to perform a first initial implant drilling 54. The user has changed the position and a stop of the initial guide bore 53 to obtain the ready made first guide bore 31, wherein the position of the implant drilling has also been changed by changing the position and the length of the implant drilling has been increased by a smaller stop. A stop is used in a guide bore for limiting the implant drill during the drilling of the implant drilling, so that the length of the implant drilling is determined by the stop. These changes are therefore carried out to obtain the ready made implant drilling 24. Correspondingly, the remaining initial guide bores 55 and 56 are also adjusted manually by the user to obtain the ready made guide bores 32 and 34, wherein the initial implant drillings 57 and 58 are also adjusted in terms of position and length to accommodate the ready made implant drillings 26 and 28. A training data set of the neural network can thus include such manual changes by the respective user to train the neural network accordingly.

REFERENCE SYMBOLS

1 Drilling template
2 Dental camera
3 Dental situation
4 Teeth
5 3D surface model
6 CT X-ray device
7 Volumes
8 Tooth roots
9 Dental nerves
10 Jawbones
11 Volume model
12 Computer
13 Display device
14 Keyboard
15 Mouse
16 Implant-supported full crown
17 Implant
18 Implant-supported bridge
19 Implant
20 Arrow
21 Arrow
22 Cursor
23 First position
24 First implant drilling
25 Second position
26 Second implant drilling
27 Third implant drilling
28 Fourth implant drilling
29 Selection menu
30 3D model
31 Guide bore
32 Guide bore
33 Guide bore
34 Guide bore
35 Contact surface
36 Contact surface
40 Contact surface
41 Neighboring teeth
42 Screw
43 Jaw
44 Drilling sleeve
45 Central axis
46 Molars
47 Undercuts
50 Initial suggestion
51 External dimensions
52 Arrow
53 Initial guide bore
54 Initial implant drilling
55 Initial guide bore
56 Initial guide bore
57 Initial implant drilling
58 Initial implant drilling

The invention claimed is:

1. A method for designing a drilling template, wherein a dental situation is measured by means of a 3D surface measuring device and a 3D surface model of the dental situation is produced and/or measured by means of an X-ray device or an MRI device, wherein the dental situation is measured and a volume model of the dental situation is produced, the method comprising the steps of:
applying an artificial neural network for machine learning (convolutional neural network; CNN) to the 3D surface model of the dental situation and/or the volume model of the dental situation and/or to an initial 3D model of the drilling template; and
automatically producing a ready made 3D model of the drilling template.

2. The method according to claim 1, further comprising the step of training the neural network on the basis of a training data set, wherein the training data set includes manual changes of several initial 3D models of drilling templates of at least one user, wherein the manual changes can be carried out by the user when designing the 3D model of the respective drilling template.

3. The method according to claim 1, further comprising the step of training the neural network on the basis of a training data set, wherein the training data set includes several 3D surface models and/or volume models of the dental situations and the corresponding 3D models of the ready made drilling templates of at least one user.

4. The method according to claim 1, further comprising the step of training the neural network on the basis of a training data set, wherein the training data set includes at least several initial 3D models of the drilling templates and corresponding ready made 3D models of the drilling templates of a user.

5. The method according to claim 2, wherein the training data set includes only the data of one user or a group of experienced users.

6. The method according to claim 2, wherein the neural network remains unchanged after training on the basis of the training data set.

7. The method according to claim 2, comprising the step of adding new data to the training data set, so that the neural network is trained further on the basis of the expanded training data set.

8. The method according to claim 6, wherein the 3D surface model of the dental situation has at least one area for an implant supply with implants to be inserted, at least one neighboring tooth, and/or an implant-supported mesostructure.

9. The method according to claim 1, wherein the neural network automatically defines a material, a production process, and/or an insertion method for the drilling template to be produced.

10. The method according to claim 2, wherein the training data set additionally includes a material of the drilling template, a production process, and/or an insertion method for the drilling template.

11. The method according to claim 2, wherein the training data set additionally includes a position, a shape, and/or a type of the drilling sleeves when a drilling template is designed with drilling sleeves.

12. The method according to claim 2, wherein the training data set additionally includes a shape and/or position of at least one support structure or holding structure of the drilling template to be produced.

13. The method according to claim 2, wherein the training data set additionally includes a shape and/or position of an anchoring structure for the drilling template to be produced.

14. The method according to claim 2, wherein the training data set additionally includes undercuts for anchoring the drilling template and/or additional holes with screws for fixing the drilling template.

15. The method according to claim 2, wherein the training data set additionally includes at least one guide bore of the drilling template for an implant drilling to be produced and/or a support area for supporting or fixing the drilling template and/or a screw for fixing the drilling template.

16. The method according to claim 2, wherein the training data set also includes anatomical structures in the volume model, namely jawbones, tooth roots and/or tooth nerves, which must be taken into account when designing an implant drilling.

17. A device for data processing, comprising means for performing the method according to claim 1.

18. A computer program, comprising commands which, when the computer program is executed by a computer, cause the computer to perform the method according to claim 1.

19. A non-transitory computer readable storage medium comprising commands which, when executed by a computer, cause the computer to perform the method according to claim 1.

* * * * *